US00PP26247P2

(12) United States Plant Patent
Polanco

(10) Patent No.: US PP26,247 P2
(45) Date of Patent: Dec. 22, 2015

(54) ***HAMELIA* PLANT NAMED 'GRELMSIZ'**

(50) Latin Name: *Hamelia patens*
Varietal Denomination: Grelmsiz

(71) Applicant: Martha Alicia Polanco, Needville, TX (US)

(72) Inventor: Martha Alicia Polanco, Needville, TX (US)

(73) Assignee: Greenleaf Nursery Company, Park Hill, OK (US)

( * ) Notice: Subject to any disclaimer, the term of this patent is extended or adjusted under 35 U.S.C. 154(b) by 166 days.

(21) Appl. No.: 13/998,293

(22) Filed: Oct. 18, 2013

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — C. A. Whealy

(57) ABSTRACT

A new and distinct cultivar of *Hamelia* plant named 'Grelmsiz', characterized by its outwardly spreading and mounding plant habit; freely branching habit, dense and bushy plant form; dark and light yellow green variegated leaves; freely flowering habit; orange red to red-colored flowers; and good container and garden performance.

3 Drawing Sheets

Botanical designation: *Hamelia patens.*
Cultivar denomination: 'GRELMSIZ'.

BACKGROUND OF THE INVENTION

The present invention relates to a new and distinct *Hamelia* plant, botanically known as *Hamelia patens* and hereinafter referred to by the name 'Grelmsiz'.

The new *Hamelia* plant is a naturally-occurring branch mutation of an unnamed selection of *Hamelia patens*, not patented. The new *Hamelia* plant was discovered and selected by the Inventor on a single plant within a population of plants of the unnamed selection in a controlled nursery environment in El Campo, Tex. in August, 2011.

Asexual reproduction of the new *Hamelia* plant by vegetative cuttings in a controlled environment in El Campo, Tex. since January, 2013 has shown that the unique features of this new *Hamelia* plant are stable and reproduced true to type in successive generations.

SUMMARY OF THE INVENTION

Plants of the new *Hamelia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Grelmsiz'. These characteristics in combination distinguish 'Grelmsiz' as a new and distinct *Hamelia* plant:

1. Outwardly spreading and mounding plant habit.
2. Freely branching habit, dense and bushy plant form.
3. Dark and light yellow green variegated leaves.
4. Freely flowering habit.
5. Orange red to red-colored flowers.
6. Good container and garden performance.

Plants of the new *Hamelia* can be compared to plants of the parent selection. Plants of the new *Hamelia* differ from plants of the parent selection in leaf color as plants of the parent selection have solid green (non-variegated) leaves.

Plants of the new *Hamelia* can be compared to plants of *Hamelia patens* 'Firefly', not patented. Plants of the new *Hamelia* differ primarily from plants of 'Firefly' in the following characteristics:

1. Plants of the new *Hamelia* are more compact than and not as upright as plants of 'Firefly'.
2. Plants of the new *Hamelia* and 'Firefly' differ in leaf color as plants of 'Firefly' have solid green (non-variegated) leaves.

BRIEF DESCRIPTION OF THE PHOTOGRAPHS

The accompanying colored photographs illustrate the overall appearance of the new *Hamelia* plant showing the colors as true as it is reasonably possible to obtain in colored reproductions of this type. Colors in the photographs may differ slightly from the color values cited in the detailed botanical description which accurately describe the colors of the new *Hamelia* plant.

The photograph on the first sheet is a side perspective view of a typical plant of 'Grelmsiz' grown in a container.

The photograph on the second sheet is a close-up view of a typical flowering plant of 'Grelmsiz'.

The photograph on the third sheet is a close-up view of a typical inflorescence of 'Grelmsiz'.

DETAILED BOTANICAL DESCRIPTION

The aforementioned photographs and following observations, measurements and values describe plants grown during the summer in three-gallon containers in an outdoor nursery in El Campo, Tex. and under cultural practices typical of commercial *Hamelia* production. During the production of the plants, day temperatures averaged 34° C. and night temperatures averaged 23° C. Plants were 18 months old when the photographs and the description were taken. In the description, color references are made to The Royal Horticultural Society Colour Chart, 1995 Edition, except where general terms of ordinary dictionary significance are used.

Botanical classification: *Hamelia patens* 'Grelmsiz'.

Parentage: Naturally-occurring branch mutation of an unnamed selection of *Hamelia patens*, not patented.

Propagation:

*Type*.—By vegetative cuttings.

*Time to initiate roots, summer*.—About 15 days at air temperatures about 32° C.

*Time to initiate roots, winter*.—About 25 days at air temperatures about 16° C.

*Time to produce a rooted young plant, summer*.—About 45 days at air temperatures about 32° C.

*Time to produce a rooted young plant, winter*.—About 60 days at air temperatures about 16° C.

*Root description*.—Medium in thickness, fibrous; white and brown in color.

*Rooting habit*.—Moderately freely branching; medium density.

Plant description:

*Plant and growth habit*.—Perennial shrub; outwardly spreading and mounding plant habit; moderately vigorous growth habit; freely branching habit with four lateral branches developing at every node; dense and bushy plant form.

*Plant height*.—About 25.4 cm.

*Plant diameter* (*area of spread*).—About 40.6 cm.

Lateral branch description:

*Length*.—About 18 cm to 20 cm.

*Diameter*.—About 5 mm.

*Internode length*.—About 9 cm to 10 cm.

*Aspect*.—About 60° to 70° from vertical.

*Strength*.—Moderately strong; flexible.

*Texture*.—Sparsely pubescent.

*Color, upper surface*.—Close to 172A.

*Color, lower surface*.—Close to 147C.

Leaf description:

*Arrangement*.—Four per node, whorled; simple.

*Length*.—About 11 cm.

*Width*.—About 4 cm.

*Shape*.—Oblanceolate.

*Apex*.—Acuminate.

*Base*.—Acute.

*Margin*.—Entire.

*Texture, upper and lower surfaces*.—Sparsely pubescent.

*Venation pattern*.—Pinnate; arcuate.

*Color*.—Developing and fully expanded leaves, upper surface: Close to 144A with random sectors of close to 146B; venation, close to 47A. Developing and fully expanded leaves, lower surface: Close to 146C; venation, close to 62A.

*Petioles*.—Length: About 2.2 cm. Diameter: About 2 mm. Texture, upper and lower surfaces: Smooth, glabrous. Color, upper surface: Close to 46A. Color, lower surface: Close to 48C.

Flower description:

*Flower arrangement and flowering habit*.—Single flowers arranged in compound helicoid cymes; flowers tubular with flared apices; freely flowering habit with about 35 to 50 flowers per cyme; flowers face upright, outwardly or somewhat drooping.

*Natural flowering season*.—Long flowering season, plants of the new *Hamelia* begin flowering in late spring and continue to flower until early autumn in Texas; flowers last a single day; flowers not persistent.

*Fragrance*.—None detected.

*Inflorescence diameter*.—About 8 cm.

*Inflorescence height*.—About 8 cm.

*Flower diameter, proximal*.—About 2.5 mm.

*Flower diameter, distal*.—About 5 mm.

*Flower length* (*height*).—About 2.5 cm.

*Flower buds*.—Length: About 2.3 mm. Diameter: About 2.5 mm. Shape: Tubular. Color: Close to 33A.

*Petals*.—Arrangement: Five petals in a single whorl; fused. Length: About 2.5 cm. Width: About 3 mm. Apex: Acute. Margin: Entire. Texture, inner and outer surfaces: Smooth, glabrous. Color: When opening and fully opened, inner surface: Close to 31A; color becoming closer to 45A with development. When opening and fully opened, outer surface: Close to 33A; color becoming closer to 45A with development.

*Sepals*.—Arrangement: Five sepals in a single whorl and fused into a cup-shaped calyx. Length: About 2 mm. Width: About 2 mm. Shape: Triangular. Apex: Sharply acute. Margin: Entire. Texture, inner and outer surfaces: Sparsely pubescent. Color, inner and outer surfaces: Close to 46A.

*Peduncles*.—Length: About 2 cm to 4 cm. Diameter: About 2 mm. Strength: Moderately strong, flexible. Texture: Sparsely pubescent. Color: Close to 46A.

*Pedicels*.—Length: About 1 mm. Diameter: About 1 mm. Strength: Moderately strong, flexible. Texture: Sparsely pubescent. Color: Close to 46A.

*Reproductive organs*.—Androecium: Stamen number: Five per flower. Filament length: About 1.5 mm. Filament color: Close to 19B. Anther shape: Arrow-shaped. Anther length: About 2 mm. Anther color: Close to 199C. Amount of pollen: Scarce. Pollen color: Close to 19B. Gynoecium: Pistil number: One per flower. Pistil length: About 2 cm. Style length: About 2 cm. Style color: Close to 37A. Stigma color: Close to 29D. Ovary color: Close to 37A.

*Seeds*.—Seed development has not been observed on plants of the new *Hamelia*.

Garden performance: Plants of the new *Hamelia* have been observed to have good garden performance and to tolerate wind, rain, temperatures ranging from about −6.7° C. to about 43.3° C. and to be hardy to USDA Hardiness Zone 8.

Pathogen & pest resistance: Plants of the new *Hamelia* have not been observed to be resistant to pathogens and pests common to *Hamelia* plants.

It is claimed:

1. A new and distinct *Hamelia* plant named 'Grelmsiz' as illustrated and described.

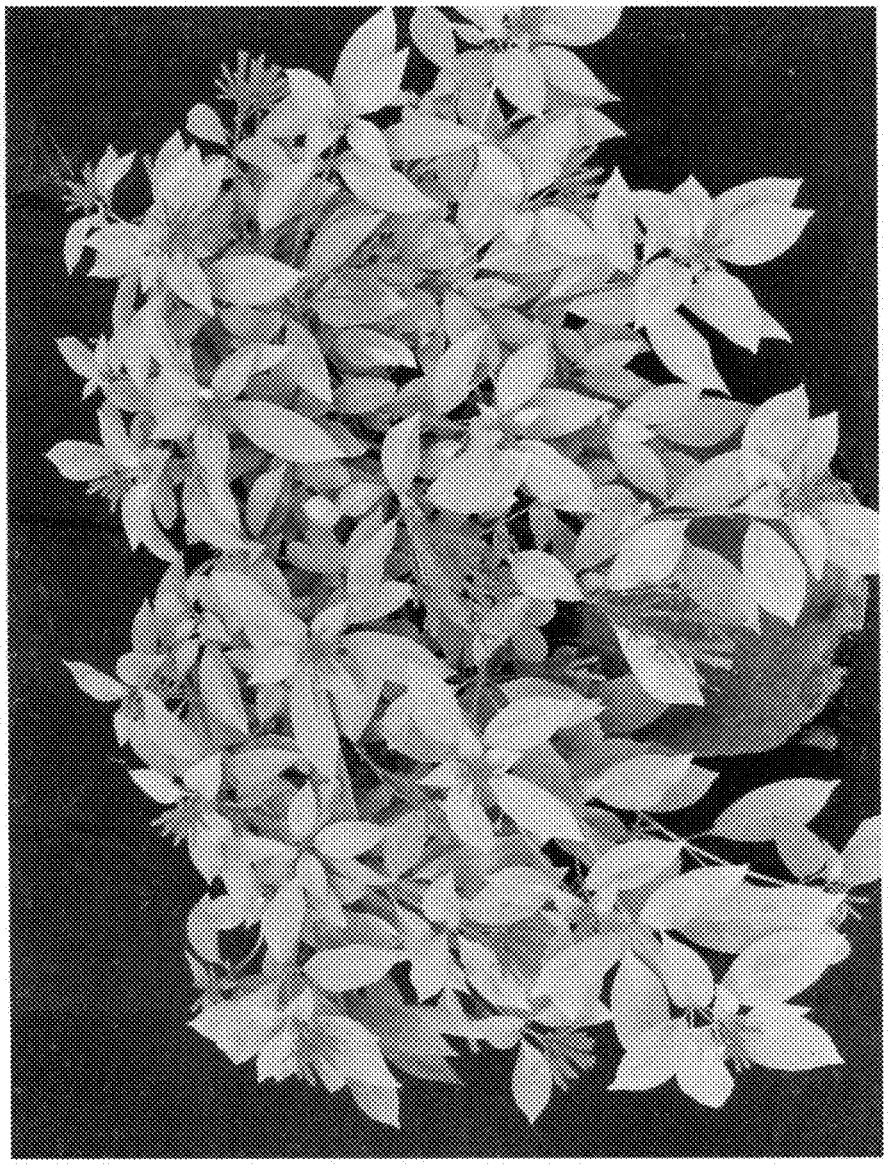

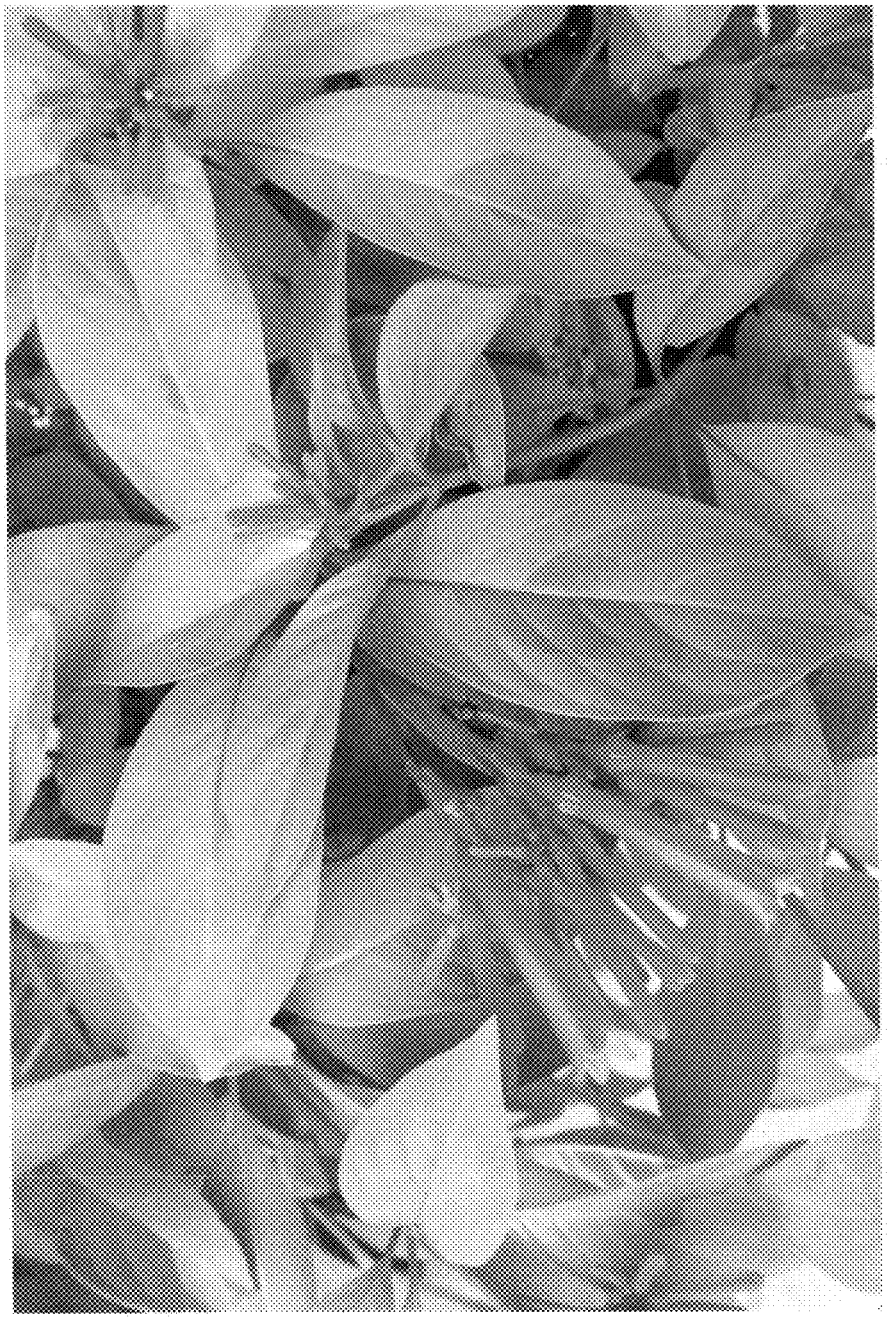

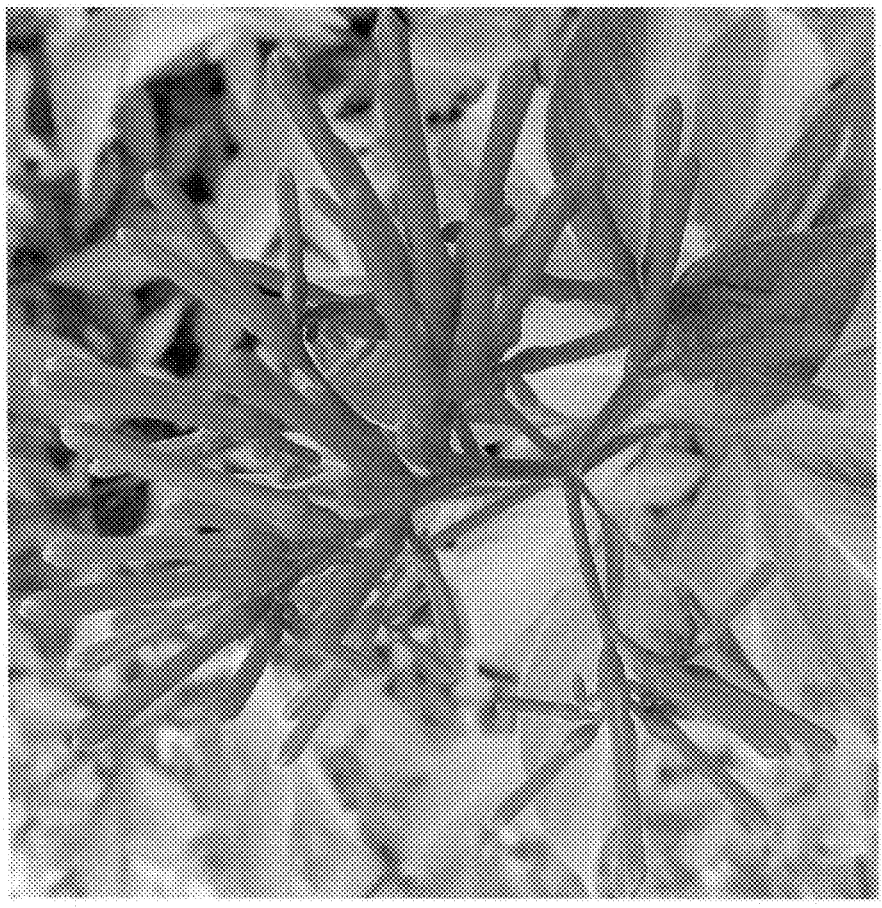

* * * * *